(12) United States Patent
Wang

(10) Patent No.: US 11,395,698 B2
(45) Date of Patent: Jul. 26, 2022

(54) SYSTEM AND METHOD FOR MEASURING HEAT TRANSFER DUE TO LOCAL TISSUE PERFUSION PRIOR TO AN ABLATION PROCEDURE

(71) Applicant: Avent, Inc., Alpharetta, GA (US)

(72) Inventor: Ruoya Wang, Decatur, GA (US)

(73) Assignee: Avent, Inc., Alpharetta, GA (US)

( * ) Notice: Subject to any disclaimer, the term of this patent is extended or adjusted under 35 U.S.C. 154(b) by 416 days.

(21) Appl. No.: 16/235,378

(22) Filed: Dec. 28, 2018

(65) Prior Publication Data

US 2020/0205893 A1   Jul. 2, 2020

(51) Int. Cl.
  *A61B 18/02*  (2006.01)
  *A61B 18/00*  (2006.01)
  *A61B 18/18*  (2006.01)

(52) U.S. Cl.
  CPC ...... *A61B 18/1815* (2013.01); *A61B 18/0218* (2013.01); *A61B 2018/00035* (2013.01);
  (Continued)

(58) Field of Classification Search
  CPC ........... A61B 2018/00005; A61B 2018/00011; A61B 2018/00017; A61B 2018/00023; A61B 2018/0243; A61B 2018/025; A61B 2018/0256; A61B 2018/0262; A61B 2018/0268; A61B 2018/0287; A61B 2018/00773; A61B 2018/00791; A61B 2018/00821; A61B 2018/00863; A61B 2018/00779; A61B 2018/00636; A61B 2018/00642; A61B 2018/00648; A61B 2018/00654; A61B 2018/00666; A61B 2018/00672; A61B 2018/00678; A61B 18/1815; A61B 18/0218; A61B 2018/00035; A61B 2018/00577; A61B 2018/126; A61B 2018/00702; A61B 2018/1253; A61B 18/16; A61B 2562/16;
  (Continued)

(56) References Cited

U.S. PATENT DOCUMENTS

| 2005/0177211 | A1* | 8/2005 | Leung | ........... | A61B 18/148 |
| | | | | | 607/101 |
| 2011/0022041 | A1* | 1/2011 | Ingle | ........... | A61B 18/1492 |
| | | | | | 606/33 |

(Continued)

OTHER PUBLICATIONS

International Search Report and Written Opinion for PCT/US2019/067056, dated Apr. 2, 2020, 14 pages.

*Primary Examiner* — Linda C Dvorak
*Assistant Examiner* — Nicholas S Borsch
(74) *Attorney, Agent, or Firm* — Meunier Carlin & Curfman LLC

(57) ABSTRACT

A system and method for performing a radiofrequency (RF) ablation procedure with a cooled RF probe includes measuring one or more local perfusion characteristics at an ablation site within a patient. The method also includes determining a heat transfer due to local perfusion at the ablation site based on the one or more local perfusion characteristics. Further, the method includes determining an operating threshold for the cooled RF probe based, at least in part, on the heat transfer. Moreover, the method includes controlling the cooled RF probe based on the operating threshold to create a lesion at the ablation site within the patient.

17 Claims, 7 Drawing Sheets

(52) U.S. Cl.
CPC .............. *A61B 2018/00577* (2013.01); *A61B 2018/00821* (2013.01)

(58) Field of Classification Search
CPC . A61B 2562/0271; A61B 18/12; A61B 18/14; A61B 2018/00714; A61B 2018/0044; A61B 2018/003398; A61B 18/1206; A61B 2018/1213; A61B 2018/122; A61B 2018/1226; A61B 18/1233; A61B 2018/124; A61B 2018/1246; A61B 2018/1266; A61B 2018/128; A61B 2018/1286; A61B 2018/1293; A61B 2018/0066; A61B 2018/00684; A61B 2018/0069; A61B 2018/00696; A61B 2018/00708; A61B 2018/0072; A61B 2018/00726; A61B 2018/00732; A61B 2018/00738; A61B 2018/00744; A61B 2018/0075; A61B 2018/00755; A61B 2018/00761; A61B 2018/00767; A61B 2018/00785; A61B 2018/00797; A61B 2018/00803; A61B 2018/00809; A61B 2018/00815; A61B 2018/00827; A61B 2018/00833; A61B 2018/00839; A61B 2018/00845; A61B 2018/00851; A61B 2018/00857; A61B 2018/00869; A61B 2018/00875; A61B 2018/0088; A61B 2018/00886; A61B 2018/00892; A61B 2018/00583; A61B 2018/1472; A61B 2218/002

See application file for complete search history.

(56) References Cited

U.S. PATENT DOCUMENTS

| | | |
|---|---|---|
| 2012/0172858 A1 | 7/2012 | Harrison et al. |
| 2016/0166309 A1 | 6/2016 | K V |
| 2018/0228402 A1 | 8/2018 | Govari |
| 2018/0344383 A1* | 12/2018 | Brannan ............ A61B 18/1206 |

\* cited by examiner

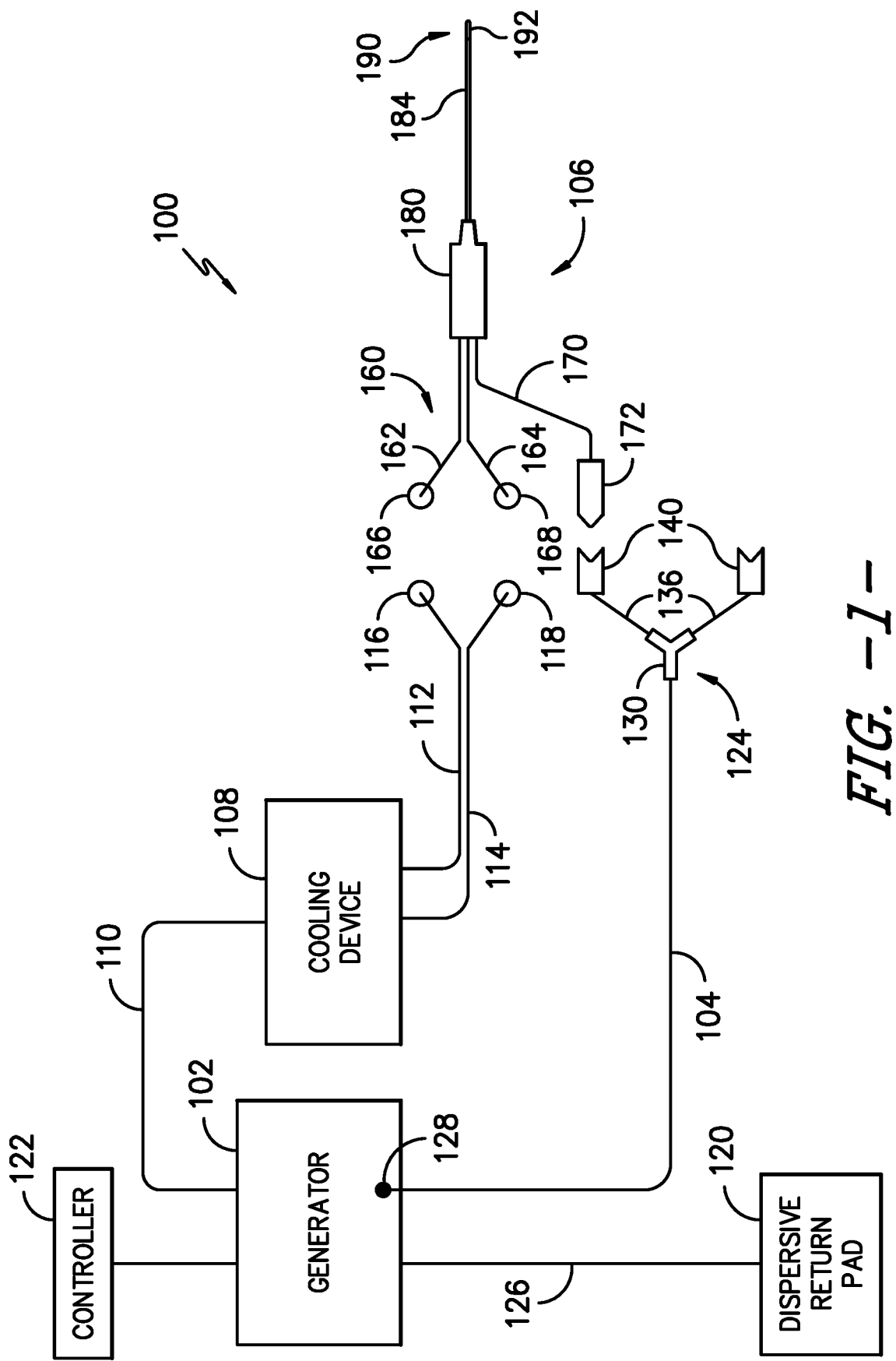
FIG. -1-

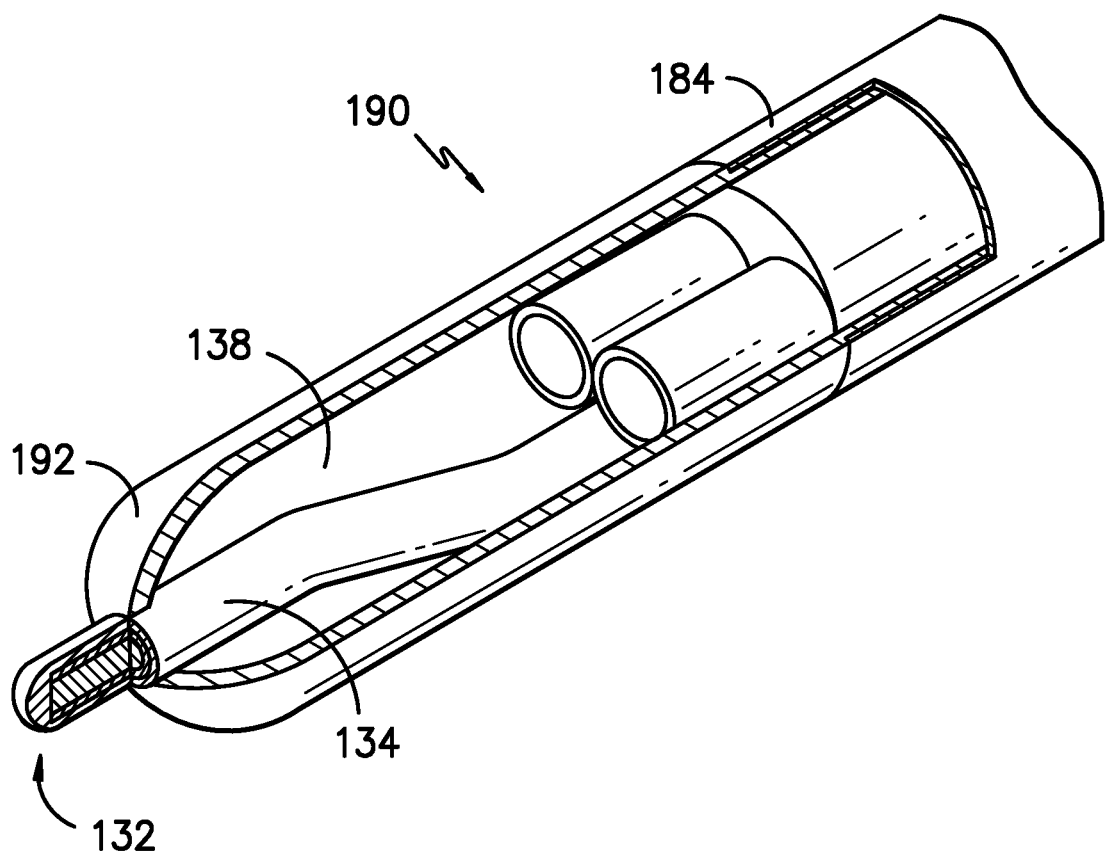
FIG. -2-

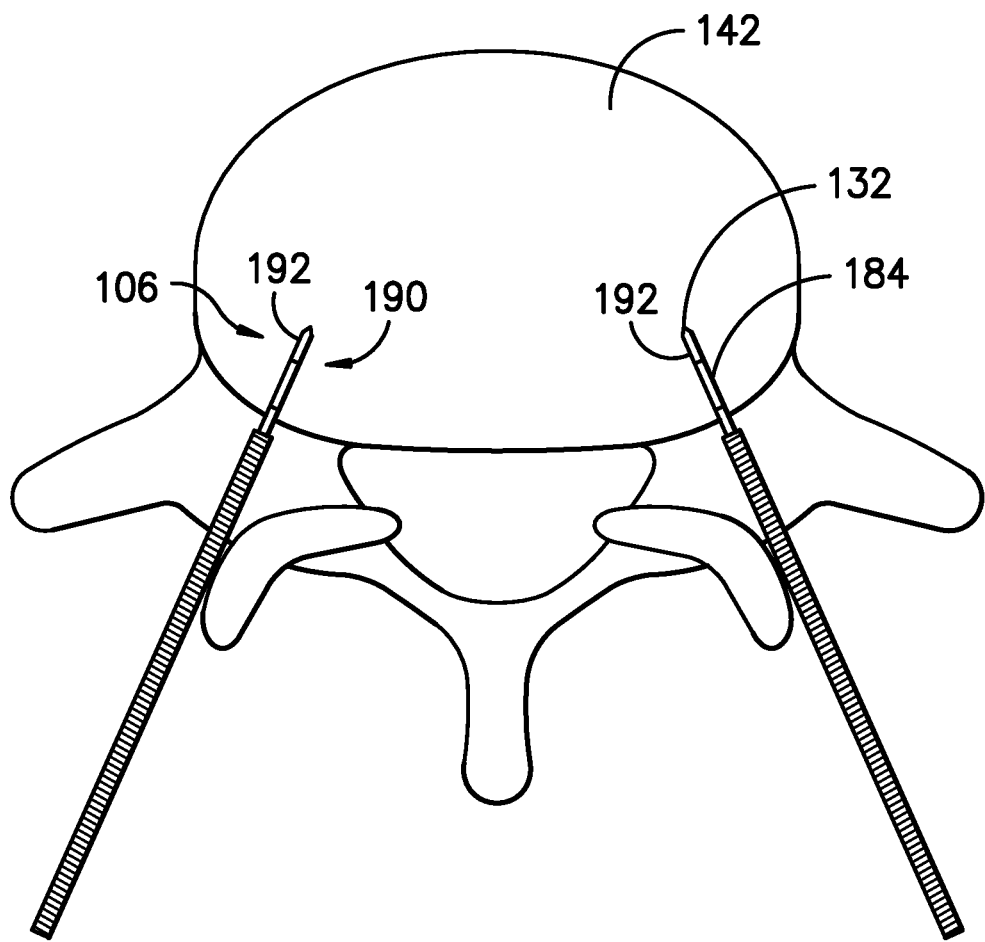
FIG. -3-

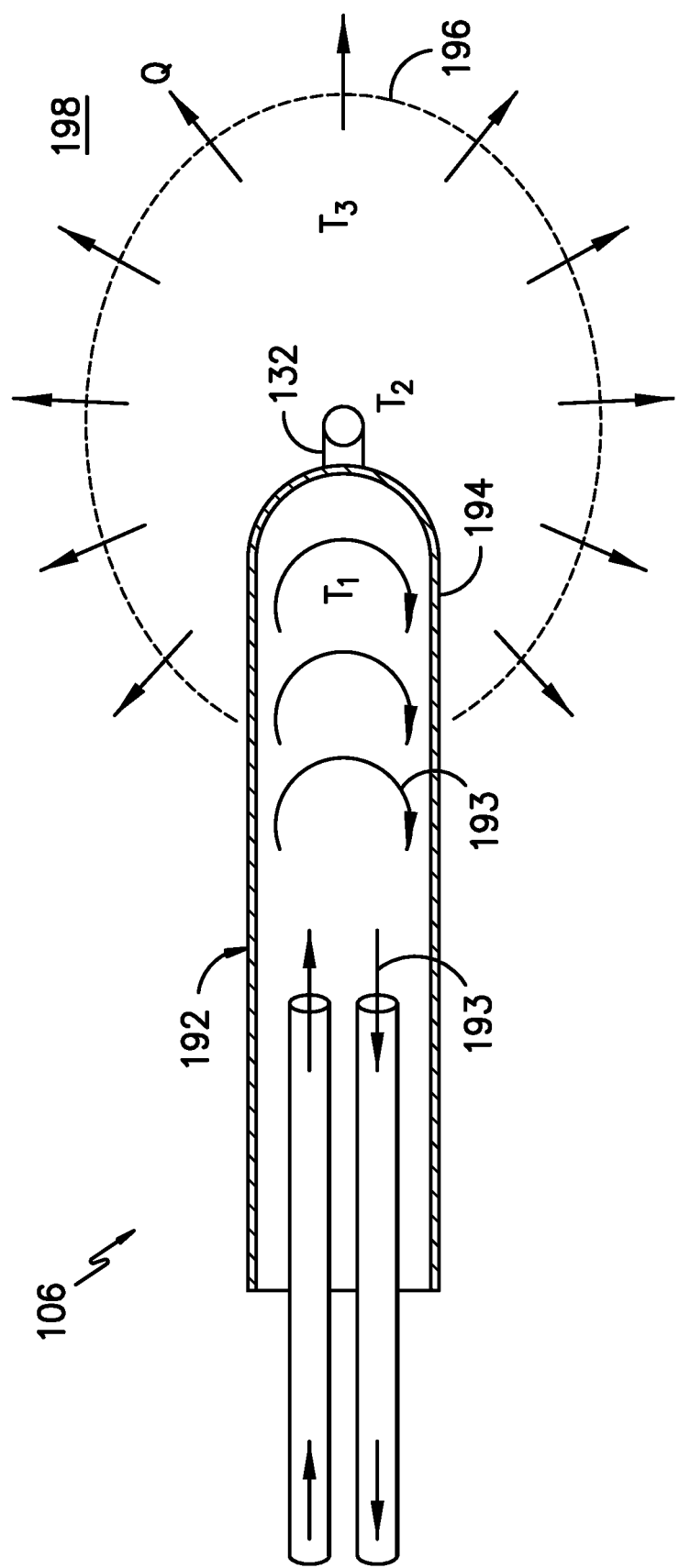
FIG. -4-

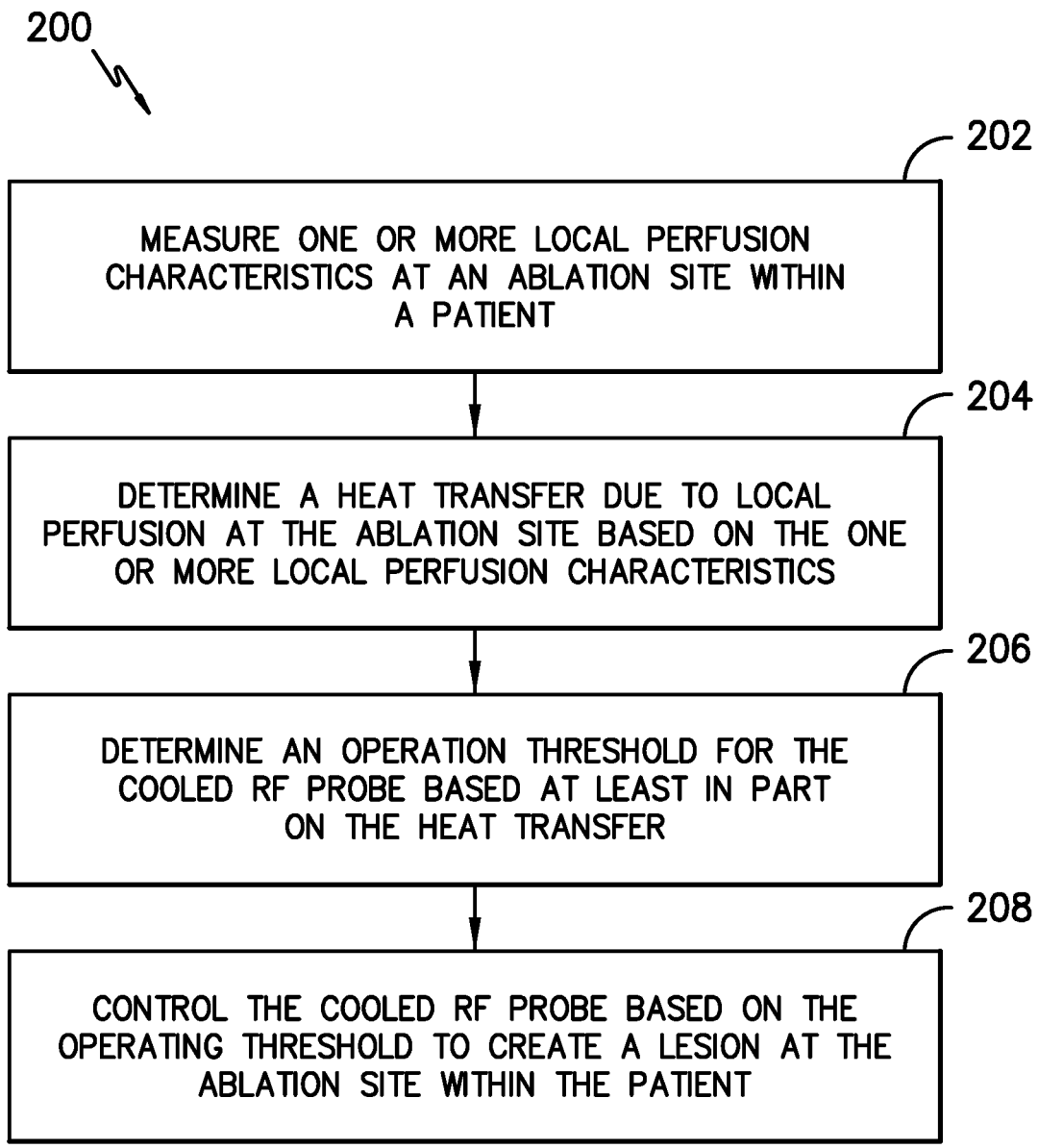
FIG. -5-

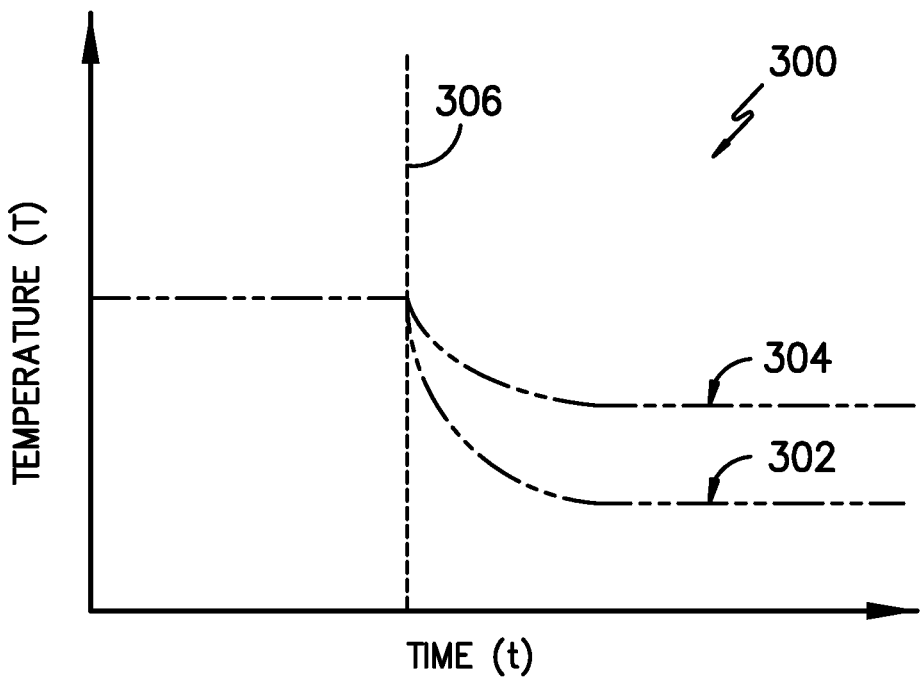
FIG. -6A-
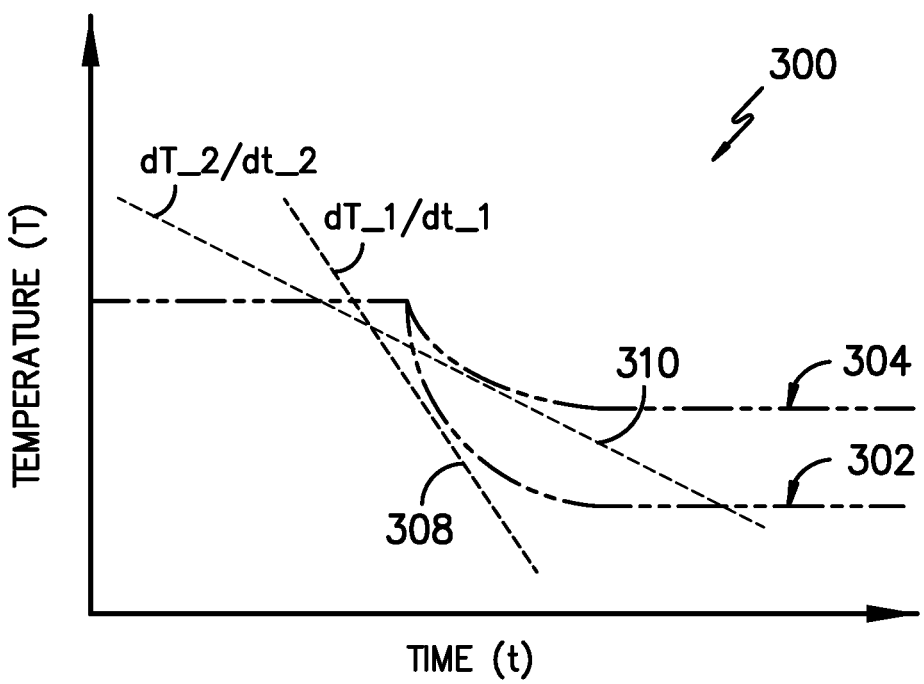
FIG. -6B-

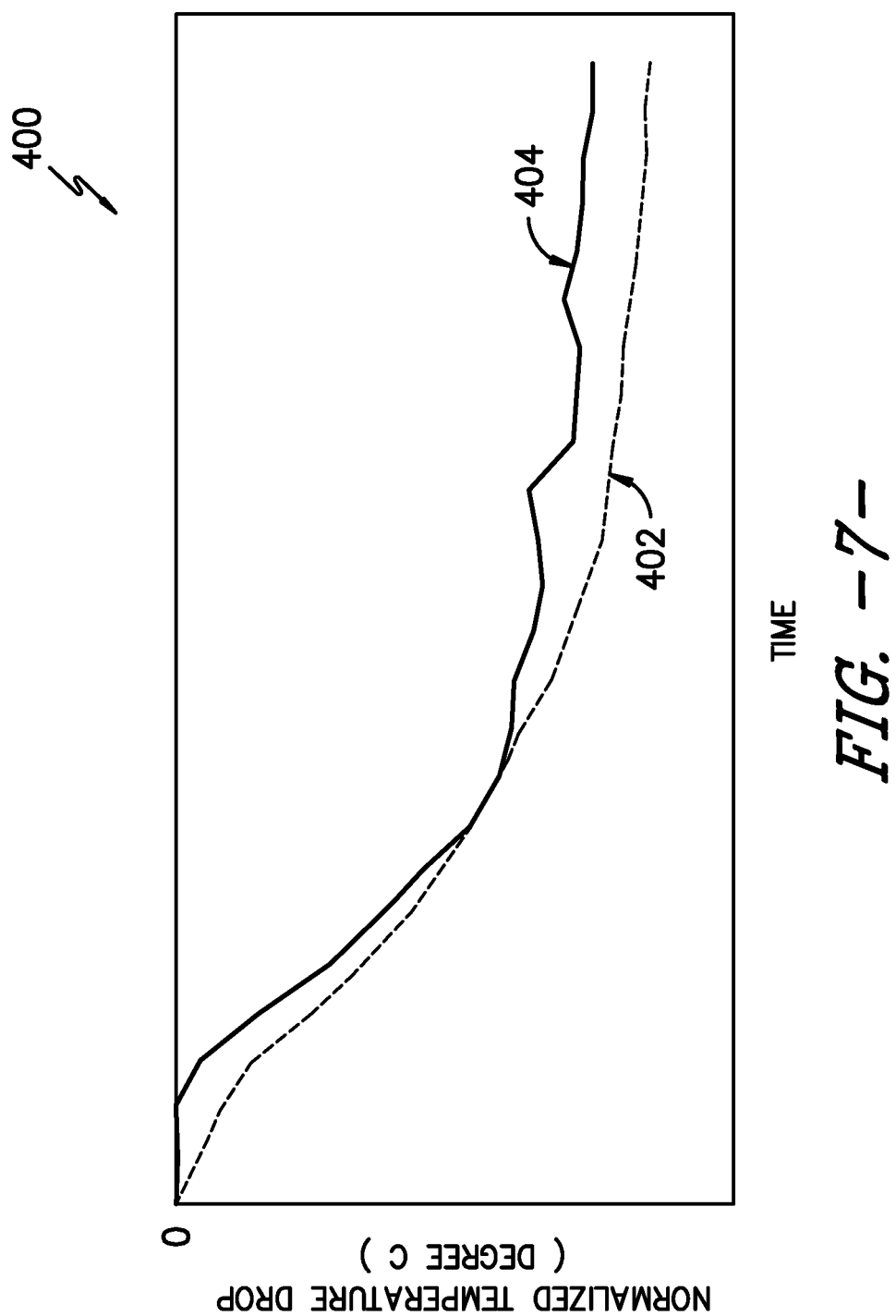

SYSTEM AND METHOD FOR MEASURING HEAT TRANSFER DUE TO LOCAL TISSUE PERFUSION PRIOR TO AN ABLATION PROCEDURE

FIELD

The present invention relates generally to radiofrequency (RF) ablation, and more particularly to a system and method for measuring heat transfer due to local tissue perfusion prior to an ablation procedure.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Radiofrequency ablation (RFA) is a minimally invasive therapy for treating chronic pain, cardiac arrhythmias, and tumors in many patients. RFA systems operate based on temperature feedback control, where RF power is modulated in order to reach a set point temperature. For instance, if the set point temperature is 60° C. and the current temperature is 50° C., power is applied until the temperature reaches 60° C. The underlying temperature-power control is based on proportional-integral-derivative (PID) control theories.

Thus, the art is continuously seeking new and improved systems and methods that continuously improve upon RFA systems. Accordingly, the present disclosure is directed to a system and method for power-/energy-based control of an RFA procedure that accounts for heat transfer due to local tissue perfusion.

SUMMARY

Objects and advantages of the invention will be set forth in part in the following description, or may be obvious from the description, or may be learned through practice of the invention.

In one aspect, the present invention is directed to a method for performing a radiofrequency (RF) ablation procedure with a cooled RF probe. The method includes measuring one or more local perfusion characteristics at an ablation site within a patient. The method also includes determining a heat transfer due to local perfusion at the ablation site based on the one or more local perfusion characteristics. Further, the method includes determining an operating threshold for the cooled RF probe based, at least in part, on the heat transfer. Moreover, the method includes controlling the cooled RF probe based on the operating threshold to create a lesion at the ablation site within the patient.

In one embodiment, the local perfusion characteristic(s) may include, for example, a steady state temperature within the cooled RF probe, a tissue temperature outside of the ablation site, a lesion temperature, a change in temperature, or an amount of perfusion.

In another embodiment, the lesion temperature is dependent on the steady state temperature and the tissue temperature. In such embodiments, the method may include determining the heat transfer due to local perfusion at the ablation site as a function of the lesion temperature.

In further embodiments, the method may include measuring the local perfusion characteristic(s) at the ablation site via one or more sensors. More specifically, the sensor(s) may include, at least, a thermocouple positioned at a distal end of the cooled RF probe. In such embodiments, the local perfusion at the ablation site actively transfers heat between the thermocouple and tissue outside of the ablation site.

In additional embodiments, determining the heat transfer due to local perfusion at the ablation site may include activating cooling flow within the cooled RF probe and generating a temperature response profile for the ablation site. In certain embodiments, if the local perfusion is below a predetermined threshold, the ablation site equilibrates to a first temperature closer to the steady state temperature within the cooled RF probe, and if the local perfusion is at or above the predetermined threshold, the ablation site equilibrates to a second temperature closer to the tissue temperature outside of the ablation site. As such, the method may also include determining the heat transfer due to local perfusion at the ablation site based on a slope of the temperature response profile prior to achieving equilibrium.

In yet another embodiment, the operating threshold may include a power threshold and/or a deposited or total energy threshold.

In another aspect, the present disclosure is directed to a radiofrequency (RF) ablation system for performing an RF ablation procedure. The RF ablation system includes an energy source for delivering energy to a patient's body, one or more energy delivery devices electrically coupled to the energy source, one or more sensors for measuring at least one local perfusion characteristic at an ablation site within the patient, and at least one processor configured to perform a plurality of operations. The plurality of operations include, for example, determining a heat transfer due to local perfusion at the ablation site based on the at least one local perfusion characteristic, determining an operating threshold for the one or more energy delivery devices based, at least in part, on the heat transfer, and controlling the one or more energy delivery devices based on the operating threshold to create a lesion at the ablation site within the patient. It should also be understood that the RF ablation system may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a portion of one embodiment of a system for applying radiofrequency electrical energy to a patient's body according to the present disclosure;

FIG. 2 illustrates a perspective cut-away view of one embodiment of a distal tip region of a probe assembly according to the present disclosure;

FIG. 3 illustrates two probes placed within an intervertebral disc to perform a radiofrequency ablation procedure according to the present disclosure;

FIG. 4 illustrates a schematic diagram of one embodiment of a distal tip region of a probe assembly according to the present disclosure;

FIG. 5 illustrates a flow chart of one embodiment of a method for performing an RF ablation procedure with a cooled RF probe according to the present disclosure;

FIG. 6A illustrates a graph of one embodiment of temperature (y-axis) versus time (x-axis) according to the present disclosure;

FIG. 6B illustrates a graph of one embodiment of temperature (y-axis) versus time (x-axis) according to the present disclosure, particularly illustrating the slope of the curves;

FIG. 7 illustrates a graph of one embodiment of normalized temperature drop (y-axis) versus time (x-axis) for an experimental test according to the present disclosure.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

Referring now to the drawings, FIG. 1 illustrates a schematic diagram of one embodiment of a radiofrequency (RF) ablation system 100 for performing an RF ablation procedure according to the present invention. As shown, the ablation system 100 includes an energy source 102 for delivering energy to a patient's body, a plurality of probe assemblies 106 (only one of which is shown) electrically coupled to the energy source 102 via one or more cables 104, a dispersive return pad 120 electrically coupled to the energy source 102, one or more cooling devices 108, a pump cable 110, one or more proximal cooling supply tubes 112 and one or more proximal cooling return tubes 114.

As shown in the illustrated embodiment, the energy source 102 is a radiofrequency (RF) generator, but may optionally be any power source that may deliver other forms of energy, including but not limited to microwave energy, thermal energy, ultrasound and optical energy. Further, the energy source 102 may include a display incorporated therein. The display may be operable to display various aspects of a treatment procedure, including but not limited to any parameters that are relevant an ablation procedure, such as temperature, impedance, etc. and errors or warnings related to a treatment procedure. If no display is incorporated into the energy source 102, the energy source 102 may include means of transmitting a signal to an external display. In one embodiment, the energy source 102 is operable to communicate with one more devices, for example with one or more of the probe assemblies 106 and/or the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 136 such that the probe assemblies 106 can be connected thereto. A proximal end 128 of the cable 104 is connected to the energy source 102. This connection can be permanent, whereby, for example, the proximal end 128 of the cable 104 is embedded within the energy source 102, or temporary, whereby, for example, the proximal end 128 of cable 104 is connected to energy source 102 via an electrical connector. The two or more distal ends 136 of the cable 104 terminate in connectors 140 operable to couple to the probe assemblies 106 and establish an electrical connection between the probe assemblies 106 and the energy source 102. In alternate embodiments, the system 100 may include a separate cable for each probe assembly 106 being used to couple the probe assemblies 106 to the energy source 102. Alternatively, the splitter 130 may include more than two distal ends. Such a connector is useful in embodiments having more than two devices connected to the energy source 102, for example, if more than two probe assemblies are being used.

The cooling device(s) 108 may include any means of reducing a temperature of material located at and proximate to one or more of the probe assemblies 106. For example, the cooling devices 108 may include a pump assembly having one or more peristaltic pumps operable to circulate a fluid from the cooling devices 108 through one or more proximal cooling supply tubes 112, the probe assemblies 106, one or more proximal cooling return tubes 114 and back to the one or more cooling devices 108.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114.

In one embodiment, the proximal supply tube connectors 116 are female luer-lock type connectors and the proximal return tube connectors 118 are male luer-lock type connectors although other connector types are intended to be within the scope of the present invention.

The probe assembly 106 may also include a proximal region 160, a handle 180, a hollow elongate shaft 184, and a distal tip region 190 that includes the one or more energy delivery devices 192. Further, as shown, the proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106, but alternate embodiments with rigid tubes are possible.

The probe cable connector 172 may be located at a proximal end of the probe assembly cable 170 and may be operable to reversibly couple to one of the connectors 140, thus establishing an electrical connection between the energy source 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the energy source 102 to the one or more energy delivery devices 192 as well as to connect multiple temperature sensing elements to the energy source 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc; however, different sizes of active regions, all of which are within the scope of the present invention, may be used depending on the specific procedure being performed. In some embodiments, feedback from the energy source 102 may automatically adjust the exposed area of the energy delivery device 192 in response to a given measurement such as impedance or temperature.

Still referring to FIG. 1, the ablation system 100 may also include a controller 122 for facilitating communication between the energy source 102, the dispersive return pad 120, and/or the cooling devices 108. In this way, feedback control is established between the cooling devices 108 and the energy source 102. The feedback control may include the energy source 102, the probe assemblies 106, the dispersive return pad 120, and/or the cooling devices 108, although any feedback between any two devices is within the scope of the present invention. The feedback control may be implemented, for example, in a control module which may be a component of the energy source 102. In such embodiments, the energy source 102 is operable to communicate bi-directionally with the probe assemblies 106 as well as with the dispersive return pad 120 and/or the cooling devices 108. In the context of this invention, bi-directional communication refers to the capability of a device to both receive a signal from and send a signal to another device.

Referring now to FIG. 2, the energy delivery devices 192 may also include a temperature sensing element 132 that protrudes beyond a distal end thereof. More specifically, as shown, the temperature sensing element 132 may have a length 414 of less than about 1 millimeter (mm) that extends from a distal end 194 of the energy delivery device 192. Accordingly, the temperature sensing elements 132 are configured to control and optimize the size of the lesion for different anatomical locations, for instance creating smaller lesions in regions adjacent to critical structures such as arteries and motor nerves.

In addition, the temperature sensing element 132 is configured to increase (or decrease) a power demand of the energy delivery device 192. Further, as shown, the temperature sensing element 132 may include a stainless steel hypotube 134 that is electrically conductive and may be electrically coupled to the energy delivery device 192. Thus, in such an embodiment, whereby energy may be conducted to the protrusion and delivered from the protrusion to surrounding tissue, the protrusion may be understood to be a component of both temperature sensing element 132 as well as the one or more energy delivery devices 192. Placing the temperature sensing elements 132 at this location, rather than within a lumen 138 defined by the energy delivery device 192, is beneficial because it allows the temperature sensing element 132 to provide a more accurate indication of the temperature of tissue proximate to the energy delivery device 192. This is due to the fact that, when extended beyond the energy delivery device 192, the temperature sensing element 132 will not be as affected by the cooling fluid flowing within the lumen 138 as it would be were it located within lumen 138. Thus, in such embodiments, the probe assembly 106 includes a protrusion protruding from the distal region of the probe assembly, whereby the protrusion is a component of the temperature sensing element 132.

Referring now to FIG. 3, in one embodiment, the first and second probe assemblies 106 may be operated in a bipolar mode. For example, as shown, FIG. 3 illustrates one embodiment of two probe assemblies 106, wherein the distal tip regions 190 thereof are located within an intervertebral disc 142. In such embodiments, electrical energy is delivered to the first and second probe assemblies 106 and this energy is preferentially concentrated therebetween through a region of tissue to be treated (i.e. an area of the intervertebral disc 142). The region of tissue to be treated is thus heated by the energy concentrated between first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies. For example, in some embodiments, three probe assemblies may be used and the probe assemblies may be operated in a triphasic mode, whereby the phase of the current being supplied differs for each probe assembly.

Referring now to FIG. 4, a schematic diagram of one embodiment of the probe assembly 106 having the energy delivery device 192 is illustrated. More specifically, as shown, the diagram illustrates the heat transfer between the probe assembly 106, the lesion 196, and the surrounding tissue 198 at an ablation site. Thus, as shown and described herein, the energy delivery device 192 is internally cooled by the circulation of a cooling fluid delivered therethrough (as indicated by arrows 193). Prior to the application of RF energy, the cooling fluid is at an equilibrium temperature denoted by $T\_1$. At the distal tip 194 of the energy delivery device 192, the temperature sensing element 132 measures the local lesion temperature denoted by $T\_2$. The local lesion temperature $T\_2$ is dependent upon the steady state temperature $T\_1$ of the cooling fluid within the probe assembly 106 and the physiologic tissue temperature $T\_3$, as the temperature sensing element 132 is thermally conductive to the upstream cooling fluid circulation and the tissue. Blood perfusion within the lesion zone 196 actively transfers heat (denoted as Q) between the active distal tip 194 of the energy delivery device 192 and the tissue 198. The amount of perfusion can vary widely depending on the local vascularization within the patient.

As such, the present invention is directed to a system and method for performing an RF ablation procedure with the probe assembly 106 described herein that accounts for local perfusion. More specifically, as shown in FIG. 5, a flow diagram of one embodiment of the method 200 is illustrated. In general, the method 200 will be described herein with reference to the probe assembly 106 shown in FIGS. 1-4. However, it should be appreciated that the disclosed method 200 may be implemented with probe assemblies having any other suitable configurations. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown at (202), the method 200 includes measuring one or more local perfusion characteristics at an ablation site within the patient. For example, in one embodiment, the local perfusion characteristic(s) may include, for example, a steady state temperature within the probe assembly 106 (e.g. $T\_1$), a tissue temperature outside of the ablation site (e.g. $T\_3$), a lesion temperature (e.g. $T\_2$), a change in temperature, or an amount of perfusion. As such, in certain embodiments, the method 200 may include measuring the local perfusion characteristic(s) at the ablation site via one or more sensors. More specifically, the sensor(s) may include, at least, the temperature sensing element 132 described herein.

As shown at (204), the method 200 also includes determining a heat transfer due to local perfusion at the ablation site based on the local perfusion characteristic(s). For example, the local perfusion at the ablation site actively transfers heat between the temperature sensing element 132 and tissue outside of the ablation site. As such, in certain embodiments, the lesion temperature may be dependent on the steady state temperature and the tissue temperature. Thus, in such embodiments, the method 200 may include determining the heat transfer due to local perfusion at the ablation site as a function of the lesion temperature.

More specifically, in one embodiment, the controller 122 is configured to determine the heat transfer due to local perfusion at the ablation site by activating cooling flow within the probe assembly 106 and generating a temperature response profile 300 (see, e.g. FIGS. 6A and 6B) for the ablation site. For example, as shown in FIGS. 6A and 6B, the graphs illustrate the process used to assess local perfusion characteristics at the ablation site. More specifically, FIG. 6A illustrates a graph of one embodiment of temperature (y-axis) versus time (x-axis). The curve 302 illustrates the temperature-time profile for the low perfusion ablation zone, whereas curve 304 illustrates the temperature-time profile for the high perfusion ablation zone. As shown at the start, both profiles 302, 304 share similar steady state temperatures, which equilibrate near physiological tissue temperature $T\_3$. At time 306, the pump of the probe assembly 106 is activated and cooling fluid is transferred to the active tip 194 of the energy delivery device 192. Thus, as shown, the ablation zone with the low perfusion 302 (e.g. local perfusion below a predetermined threshold) equilibrates to a first temperature closer to the cooling flow temperature $T\_1$. In contrast, as shown, the ablation zone with the high perfusion 304 (e.g. local perfusion above the predetermined threshold) equilibrates to a second temperature closer to physiological tissue temperature $T\_3$. Referring particularly to FIG. 6B, the slopes 308, 310 of the temperature response profile 300 prior to achieving equilibrium is indicative of the local heat transfer capacity. Thus, higher local perfusion 308 results in a shallower equilibration slope than lower local perfusion 310.

Referring back to FIG. 5, as shown at (206), the method 200 further includes determining an operating threshold for the probe assembly 106 based, at least in part, on the heat transfer capacity due to the local perfusion. For example, in particular embodiments, the operating threshold may include a power threshold and/or a deposited or total energy threshold. In certain embodiments, the power threshold or total deposited energy can be a better predictor of the lesion creation process, thereby resulting in more consistent lesion size if the ablation procedure is also power- or total-energy-threshold controlled. By considering the local perfusion surrounding the ablation site, the power/energy-based control is more accurate.

Accordingly, as shown at (208), the method 200 includes controlling the probe assembly 106 based on the operating threshold to create a lesion at the ablation site within the patient. For example, in one embodiment, the slope value can be used by the controller 122 to compensate for heat loss due to the perfusion during power/total energy feedback control routines of the probe assembly 106.

Referring now to FIG. 7, a graph 400 of one embodiment of the normalized temperature drop (y-axis) versus time (x-axis) to depict experimental results of the method described herein is illustrated. As shown, the temperature-time profile was generated using the probe assembly 106 described herein in a water bath that was heated to 37° C. In the low perfusion experimental case (as denoted by 402), the water bath was not stirred. In the high perfusion experimental case (as denoted by 404), the water bath was stirred to mimic blood perfusion at the ablation site. The results illustrate that for high perfusion 404, the temperature equilibrates more rapidly to a higher equilibrium temperature than the low perfusion case 402.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for performing a radiofrequency (RF) ablation procedure with a cooled RF probe, the method comprising:
   determining local perfusion characteristics at an ablation site within a patient by measuring, via one or more sensors including a thermocouple protruding beyond a distal end of the cooled RF probe, a steady-state temperature within the cooled RF probe and a lesion temperature at the ablation site, the local perfusion characteristics comprising i) the steady-state temperature within the cooled RF probe, ii) a temperature of the tissue outside of the ablation site, and iii) the lesion temperature at the ablation site, wherein the lesion temperature at the ablation site is dependent on the steady-state temperature within the cooled RF probe and the temperature of the tissue outside of the ablation site;
   generating a temperature response profile by activating a flow of cooling fluid within the cooled RF probe and subsequently monitoring the local perfusion characteristics over a time period, wherein a slope of the temperature response profile defines a rate of heat transfer due to local perfusion at the ablation site;
   determining an operating threshold for the cooled RF probe based on the temperature response profile, wherein the operating threshold compensates for heat loss due to the local perfusion based on the slope of the temperature response profile; and
   controlling the cooled RF probe to create a lesion at the ablation site within the patient by applying RF energy at the operating threshold.

2. The method of claim 1, wherein the lesion temperature is dependent on the steady-state temperature within the cooled RF probe and the temperature of the tissue outside of the ablation site.

3. The method of claim 1, wherein the local perfusion at the ablation site actively transfers heat between the thermocouple and the tissue outside of the ablation site.

4. The method of claim 1, wherein the ablation site is determined to have low perfusion if the temperature of the tissue at the ablation site equilibrates to the steady state temperature within the cooled RF probe.

5. The method of claim 1, wherein the slope of the temperature response profile is determined prior to the temperature of the tissue outside of the ablation site reaching equilibrium.

6. The method of claim 1, wherein the operating threshold comprises at least one of a power threshold or a deposited energy threshold.

7. A radiofrequency (RF) ablation system for performing an RF ablation procedure, the RF ablation system comprising:
   an energy source for delivering energy to a patient's body;
   a cooled RF probe electrically coupled to the energy source;
   one or more sensors for measuring local perfusion characteristics at an ablation site within the patient, the local perfusion characteristics including i) a steady-state temperature within the cooled RF probe, ii) a temperature of a tissue outside of the ablation site, and iii) a lesion temperature at the ablation site, the one or more sensors including a thermocouple protruding beyond a distal end of the cooled RF probe; and
   at least one processor configured to perform a plurality of operations, the plurality of operations comprising:
      generating a temperature response profile by activating a flow of cooling fluid within the cooled RF probe and subsequently monitoring the local perfusion characteristics over a time period, wherein a slope of the temperature response profile defines a heat transfer due to local perfusion at the ablation site;
      determining an operating threshold for the cooled RF probe based on the temperature response profile, wherein the operating threshold compensates for heat loss due to the local perfusion based on the slope of the temperature response profile; and
      controlling the cooled RF probe to create a lesion at the ablation site within the patient by applying RF energy at the operating threshold.

8. The RF ablation system of claim 7, wherein the cooled RF probe comprises a proximal end and a distal end, the distal end comprising an active distal tip.

9. The RF ablation system of claim 7, wherein the ablation site is determined to have low perfusion if the temperature of the tissue outside of the ablation site equilibrates to the steady state temperature within the cooled RF probe.

10. The RF ablation system of claim 7, wherein the slope of a temperature response profile is determined prior to the temperature of the tissue outside of the ablation site reaching equilibrium.

11. The RF ablation system of claim 7, wherein the operating threshold comprises at least one of a power threshold or a deposited energy threshold.

12. The method of claim 1, wherein the ablation site is determined to have high perfusion if the temperature of the tissue at the ablation site equilibrates to the lesion temperature at the ablation site.

13. The method of claim 1, wherein the temperature response profile is generated prior to an application of the RF energy by the cooled RF probe.

14. The method of claim 1, wherein the local perfusion characteristics are monitored until the temperature of the tissue at the ablation site reaches an equilibrium.

15. The RF ablation system of claim 7, wherein the ablation site is determined to have high perfusion if the temperature of the tissue at the ablation site equilibrates to the lesion temperature at the ablation site.

16. The RF ablation system of claim 7, wherein the temperature response profile is generated prior to an application of the RF energy by the cooled RF probe.

17. The RF ablation system of claim 7, wherein the local perfusion characteristics are monitored until the temperature of the tissue at the ablation site reaches an equilibrium.

* * * * *